US009637461B2

(12) United States Patent
Nomura et al.

(10) Patent No.: US 9,637,461 B2
(45) Date of Patent: May 2, 2017

(54) ELECTRICAL CONNECTION STRUCTURE

(71) Applicants: AUTONETWORKS TECHNOLOGIES, LTD., Yokkaichi-shi, Mie (JP); SUMITOMO WIRING SYSTEMS, LTD., Yokkaichi-shi, Mie (JP); SUMITOMO ELECTRIC INDUSTRIES, LTD., Osaka-shi, Osaka (JP); KYUSHU UNIVERSITY, NATIONAL UNIVERSITY CORPORATION, Fukuoka-shi, Fukuoka (JP)

(72) Inventors: Hideki Nomura, Yokkaichi (JP); Hiroki Hirai, Yokkaichi (JP); Junichi Ono, Yokkaichi (JP); Takuji Ootsuka, Yokkaichi (JP); Takehiro Hosokawa, Yokkaichi (JP); Tatsuya Hase, Yokkaichi (JP); Kazuo Nakashima, Yokkaichi (JP); Kazuhiro Goto, Osaka (JP); Makoto Mizoguchi, Fukuoka (JP)

(73) Assignees: AUTONETWORKS TECHNOLOGIES, LTD., Mie (JP); SUMITOMO WIRING SYSTEMS, LTD., Mie (JP); SUMITOMO ELECTRIC INDUSTRIES, LTD., Osaka (JP); KYUSHU UNIVERSITY, NATIONAL UNIVERSITY CORPORATION, Fukuoka-Shi (JP)

( * ) Notice: Subject to any disclaimer, the term of this patent is extended or adjusted under 35 U.S.C. 154(b) by 0 days.

(21) Appl. No.: 15/028,561

(22) PCT Filed: Sep. 29, 2014

(86) PCT No.: PCT/JP2014/075793
§ 371 (c)(1),
(2) Date: Apr. 11, 2016

(87) PCT Pub. No.: WO2015/056554
PCT Pub. Date: Apr. 23, 2015

(65) Prior Publication Data
US 2016/0264533 A1  Sep. 15, 2016

(30) Foreign Application Priority Data
Oct. 17, 2013 (JP) .................... 2013-216091

(51) Int. Cl.
*C07D 249/18* (2006.01)
*H01R 4/62* (2006.01)
(Continued)

(52) U.S. Cl.
CPC ............ *C07D 249/18* (2013.01); *B32B 15/01* (2013.01); *C07D 235/04* (2013.01);
(Continued)

(58) Field of Classification Search
USPC ....................................... 174/73.1
See application file for complete search history.

(56) References Cited

U.S. PATENT DOCUMENTS 3,837,833 A * 9/1974 Couture ................ C03B 23/031
65/106
6,066,796 A * 5/2000 Itoyama ............ H01L 31/02008
136/251
(Continued)

FOREIGN PATENT DOCUMENTS

JP    H05-159846 A    6/1993
JP    H07-249445 A    9/1995
(Continued)

OTHER PUBLICATIONS

October 21, 2014 Written Opinion issued in International Patent Application No. PCT/JP2014/075793.
(Continued)

*Primary Examiner* — Timothy Thompson
*Assistant Examiner* — Krystal Robinson
(74) *Attorney, Agent, or Firm* — Oliff PLC

(57) ABSTRACT

An electrical connection structure includes: a first metal member including copper or a copper alloy, a plated tin layer being formed on at least a portion of the first metal member; a second metal member that is electrically connected or connectable to the first metal member; and a surface treating layer formed on the surface of the first metal member. The surface treating layer is formed by applying a surface treating agent containing base oil and a metal affinity compound having a lipophilic group and an affinity group that
(Continued)

has an affinity for metal. The metal affinity compound contains an adduct between an acidic alkyl phosphate ester and an azole compound and an adduct between an acidic alkyl phosphate ester and a metal and/or an organic amine compound.

10 Claims, 7 Drawing Sheets

(51) Int. Cl.
| | |
|---|---|
| H01R 13/03 | (2006.01) |
| C23F 11/14 | (2006.01) |
| C23F 11/167 | (2006.01) |
| H01B 7/28 | (2006.01) |
| C23F 11/10 | (2006.01) |
| C23F 11/16 | (2006.01) |
| H01B 3/20 | (2006.01) |
| C10M 137/08 | (2006.01) |
| B32B 15/01 | (2006.01) |
| C22C 9/00 | (2006.01) |
| C22C 13/00 | (2006.01) |
| C07D 235/04 | (2006.01) |
| C07D 277/72 | (2006.01) |
| H01B 1/02 | (2006.01) |

(52) U.S. Cl.
CPC ......... *C07D 277/72* (2013.01); *C10M 137/08* (2013.01); *C22C 9/00* (2013.01); *C22C 13/00* (2013.01); *C23F 11/10* (2013.01); *C23F 11/149* (2013.01); *C23F 11/165* (2013.01); *C23F 11/1673* (2013.01); *H01B 1/023* (2013.01); *H01B 1/026* (2013.01); *H01B 3/20* (2013.01); *H01B 7/2806* (2013.01); *H01R 4/62* (2013.01); *H01R 13/03* (2013.01); *C10M 2223/043* (2013.01); *C10N 2240/202* (2013.01)

(56) References Cited

U.S. PATENT DOCUMENTS

| | | | |
|---|---|---|---|
| 6,627,329 B1 | 9/2003 | Shintani | |
| 2002/0057360 A1* | 5/2002 | Abe | H04N 5/2252 348/373 |
| 2002/0061676 A1* | 5/2002 | Kameyama | H01R 4/2429 439/404 |
| 2005/0245129 A1* | 11/2005 | Sato | H01R 9/0515 439/578 |

FOREIGN PATENT DOCUMENTS

| | | |
|---|---|---|
| JP | H10-302866 A | 11/1998 |
| JP | 2000-015743 A | 1/2000 |
| JP | 2006-176870 A | 7/2006 |
| JP | 2012-054170 A | 3/2012 |
| JP | 2013-235716 A | 11/2013 |

OTHER PUBLICATIONS

October 21, 2014 Search Report issued in International Patent Application No. PCT/JP2014/075793.

Nov. 10, 2015 Office Action issued in Japanese Patent Application No. 2013-216091.

\* cited by examiner

ELECTRICAL CONNECTION STRUCTURE

TECHNICAL FIELD

The present invention relates to an electrical connection structure.

BACKGROUND ART

In portions where two metal members are electrically connected to each other, such as a portion where a terminal and an electric wire are connected to each other or a portion where terminals are fitted to each other, there are cases where the materials constituting a terminal and an electric wire, or materials constituting a terminal and a partner terminal, or the materials of a metal plate constituting a terminal and a plated layer formed on the surface of the metal plate, include dissimilar metals.

When members made of dissimilar metals are arranged near each other in this manner, there is a concern that water attaches across the dissimilar metals, resulting in the flow of corrosion current. In order to avoid such a problem, grease or the like is applied onto a connection portion where terminals are connected to each other, for example (see Patent Document 1, for example).

CITATION LIST

Patent Documents

Patent Document 1: JP H5-159846A

As mentioned in Patent Document 1, when an oil component such as grease is applied, there is a risk that stickiness and dripping occur, thus impairing the workability and contaminating surrounding base materials. Therefore, it is necessary to apply the oil component as thinly as possible. However, if the oil component is applied too thinly, it becomes difficult to retain a stable oil film on a metal surface for a long period of time. In particular, under high temperature conditions, the oil component may be turned into low molecular weight molecules due to oxidation or volatilize, thus making it more difficult to retain a stable oil film on the metal surface. This is because the oil component does not chemically bond to the metal surface but is in intimate contact with the metal surface due to van der Waals forces, which exhibit only weak adhesive power.

Therefore, there is a need in the art to suppress the corrosion of metal members in an electrical connection structure where the metal members are electrically connected to each other.

SUMMARY

In order to solve the foregoing problems, an aspect of the present invention is an electrical connection structure including: a first metal member including copper or a copper alloy, a plated tin layer being formed on at least a portion of the first metal member; a second metal member that is electrically connected or connectable to the first metal member; and a surface treating layer formed on a surface of the first metal member, wherein the surface treating layer is formed by applying a surface treating agent containing base oil and a metal affinity compound having a lipophilic group and an affinity group that has an affinity for metal, and the metal affinity compound contains an adduct (a) between an azole compound and an acidic alkyl phosphate ester including one or more of the compounds represented by General Formula (1) and General Formula (2) below, and an adduct (b) between a metal and/or an organic amine compound and an acidic alkyl phosphate ester including one or more of the compounds represented by General Formula (1) and General Formula (2) below.

$$P(=O)(-OR_1)(-OH)_2 \tag{1}$$

$$P(=O)(-OR_1)_2(-OH) \tag{2}$$

(It should be noted that $R_1$ represents an organic group having 4 or more carbon atoms.)

In the electrical connection structure according to an aspect of the present invention where the first metal member and the second metal member are electrically connected to each other, the surface treating layer is formed, by applying a surface treating compound containing the metal affinity compound and the base oil, on the first metal member including copper or a copper alloy (referred to also as "copper (alloy)" hereinafter) on which the plated tin layer is formed.

The lipophilic group of the metal affinity compound contained in the surface treating compound binds to the base oil. On the other hand, it is conceivable that the affinity group of the adduct (a) between an acidic alkyl phosphate ester and an azole compound included in the metal affinity compound preferentially binds to copper included in the first metal member, and the affinity group of the adduct (b) between a metal and/or an organic amine compound and an acidic alkyl phosphate ester preferentially binds to tin contained in the plated tin layer.

That is, with the present invention, the surface treating layer containing a base oil component is stably retained on the surface of the first metal member. Therefore, even when water adheres across the copper (alloy) included in the first metal member and the plated tin layer and across the first metal member and the second metal member, it is possible to suppress the flow of the corrosion current. As a result, with the present invention, it is possible to suppress the corrosion of the metal members in the electrical connection structure where the metal members are electrically connected to each other.

DESCRIPTION OF EMBODIMENTS

Embodiment 1

Figure 1:
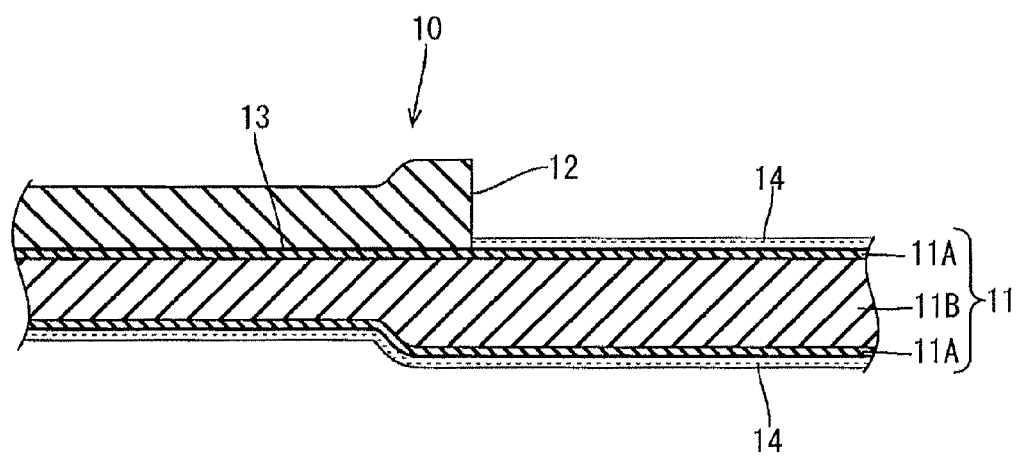
FIG. 1 is an enlarged cross-sectional view showing an electrical connection structure according to Embodiment 1 of the present invention.

An electrical connection of Embodiment 1 according to the present invention will be described with reference to FIG. 1. In this embodiment, the electrical connection structure 10 is constituted by two metal members 11 and 12 (namely a first metal member 11 and a metal member 12).

First Metal Member 11

The first metal member 11 is constituted by a plate material 11B including copper or a copper alloy, and a plated tin layer 11A is formed on its surface. In this embodiment, the first metal member 11 is obtained by pressing, into a predetermined shape, the plate material 11B including copper (alloy) on which the plated tin layer 11A is formed.

Second Metal Member 12

A second metal member 12 includes a metal having an ionization tendency larger than that of copper. Examples of the metal included in the second metal member 12 include magnesium, aluminum, manganese, zinc, chromium, iron, cadmium, cobalt, nickel, tin, and lead, or an alloy thereof. In this embodiment, the second metal member 12 is obtained by pressing a plate material including aluminum or an aluminum alloy into a predetermined shape.

Electrical Connection Structure 10

As a method for connecting the first metal member 11 and the second metal member 12, any method such as resistance welding, ultrasonic welding, brazing (including brazing and soldering), cold welding, pressure welding, or bolting can be selected as appropriate. In this embodiment, the first metal member 11 and the second metal member 12 are pressure-welded to each other by being sandwiched between a pair of jigs (not shown). The first metal member 11 and the second metal member 12 are electrically connected to each other in a connection portion 13 where the first metal member 11 and the second metal member 12 are connected to each other by pressure welding.

Surface Treating Layer 14

A surface treating layer 14 is formed on the surface of the first metal member 11. The surface treating layer 14 is formed on a portion of the surface of the first metal member 11 other than the connection portion 13 where the first metal member 11 is in contact with the second metal member 12. The surface of the first metal member 11 refers to all the surfaces exposed to the outside, such as the upper surface, the lower surface, and the side surfaces of the first metal member 11. The surface treating layer 14 according to this embodiment is formed on at least the first metal member 11.

The surface treating layer 14 is formed by applying a surface treating agent containing base oil and a metal affinity compound having a lipophilic group and an affinity group that has an affinity for metal.

The metal affinity compound has an oil film retention function, for being added to base oil to be applied onto the surface of the first metal member 11 and retaining the base oil on the surface of the member. Specifically, the metal affinity compound contains an adduct (a) between an azole compound and an acidic alkyl phosphate ester including one or more of the compounds represented by General Formula (1) and General Formula (2) below, and an adduct (b) between a metal and/or an organic amine compound and an acidic alkyl phosphate ester including one or more of the compounds represented by General Formula (1) and General Formula (2) below.

$$P(=O)(-OR_1)(-OH)_2 \quad (1)$$

$$P(=O)(-OR_1)_2(-OH) \quad (2)$$

(It should be noted that $R_1$ represents an organic group having 4 or more carbon atoms.)

Examples of the adduct (a) include a compound constituted by only an adduct between a compound represented by General Formula (1) and an azole compound, a compound constituted by only an adduct between a compound represented by General Formula (2) and an azole compound, and a compound constituted by only an adduct between a compound represented by General Formula (1) and an azole compound and an adduct between a compound represented by General Formula (2) and an azole compound.

Examples of the adduct (b) include a compound constituted by only an adduct between a compound represented by General Formula (1) and a metal, a compound constituted by only an adduct between a compound represented by General Formula (1) and an organic amine compound, a compound constituted by only an adduct between a compound represented by General Formula (1) and a metal and an adduct between a compound represented by General Formula (1) and an organic amine compound, a compound constituted by only an adduct between a compound represented by General Formula (2) and a metal, a compound constituted by only an adduct between a compound represented by General Formula (2) and an organic amine compound, a compound constituted by only an adduct between a compound represented by General Formula (2) and a metal and an adduct between a compound represented by General Formula (2) and an organic amine compound, a compound constituted by only an adduct between a compound represented by General Formula (1) and a metal and an adduct between a compound represented by General Formula (2) and a metal, and a compound constituted by only an adduct between a compound represented by General Formula (1) and an organic amine compound and an adduct between a compound represented by General Formula (2) and an organic amine compound.

Examples of the acidic alkyl phosphate ester include a compound constituted by only a compound represented by General Formula (1), a compound constituted by only a compound represented by General Formula (2), and a compound constituted by only a compound represented by General Formula (1) and a compound represented by General Formula (2).

In the acidic alkyl phosphate ester, $R_1$ is constituted by an organic group having 4 or more carbon atoms. The acidic alkyl phosphate ester has an organic group having a certain number of carbon atoms, and thus has an excellent compatibility with base oil that is a long-chain alkyl compound. Therefore, the acidic alkyl phosphate ester improves the compatibility between the metal affinity compound and the base oil. This makes it possible for the acidic alkyl phosphate ester to make a mixture of the metal affinity compound and the base oil into a liquid form. Accordingly, the acidic alkyl phosphate ester imparts favorable application properties for the metal surface to a surface treating agent containing the metal affinity compound and the base oil.

From the viewpoint of excellent compatibility with the base oil, $R_1$ has preferably 4 or more carbon atoms, and more preferably 6 or more carbon atoms. On the other hand, from the viewpoint of versatility and cost, $R_1$ has preferably 30 or less carbon atoms, more preferably 26 or less carbon atoms, and even more preferably 22 or less carbon atoms.

There is no particular limitation to $R_1$ as long as $R_1$ is an organic group having 4 or more carbon atoms, and examples thereof include an alkyl group constituted by a saturated hydrocarbon, an alkenyl group constituted by an unsaturated hydrocarbon, and a hetero element-containing group. From the viewpoint of excellent compatibility with the base oil, an alkyl group constituted by a saturated hydrocarbon and an alkenyl group constituted by an unsaturated hydrocarbon are preferable as $R_1$. The alkyl group and the alkenyl group may have any of a linear structure, a branched structure, and a cyclic structure.

Examples of an acidic alkyl phosphate ester having an alkyl group as $R_1$ include butyl acid phosphate, 2-ethylhexyl acid phosphate, isodecyl acid phosphate, lauryl acid phosphate, tridecyl acid phosphate, stearyl acid phosphate, oleyl acid phosphate, isostearyl acid phosphate, and di-2-ethylhexyl acid phosphate. Of these, oleyl acid phosphate and isostearyl acid phosphate are preferable from the viewpoint in which an adduct formed has more excellent compatibility with the base oil.

Examples of the hetero element-containing group include groups containing a hetero element such as N, O, and S. Examples thereof include an alkyl chain and an alkenyl chain including an ether bond, an ester bond, an amide bond, a thioether bond, a thioester bond, or the like.

An azole compound mainly strengthens a bond to a transition metal, which has high coordinate bonding properties, due to an effect of an unshared electron pair of a nitrogen atom included in the molecule. Moreover, since an adduct between the azole compound and the acidic alkyl phosphate ester is a liquid, the azole compound can keep the metal affinity compound in a liquid form. This makes the compatibility between the metal affinity compound and the base oil favorable, thus making it possible to make a mixture of the metal affinity compound and the base oil into a liquid form. Accordingly, the azole compound imparts favorable application properties for the metal surface to the surface treating agent.

Examples of the azole compound include an azole, a diazole, a triazole and a tetrazole. More specific examples thereof include pyrrole, imidazole, pyrazole, 1,2,3-triazole, 1,2,4-triazole, tetrazole, isoindole, benzimidazole, indazole, 1H-benzotriazole, 2H-benzotriazole, imidazo[4,5-b]pyridine, indole, purine, pyrazolo[3,4-d]pyrimidine, triazolo[4,5-d]pyrimidine, and benzothiazole, or a derivative thereof. These may be used alone or in a combination of two or more. Of these, 1H-benzotriazole is preferable from the viewpoint of coordinate bonding properties for the transition metals.

Metal and an organic amine compound mainly strengthen a bond to a typical metal, which has high ion bonding properties. Although the acidic alkyl phosphate ester itself is likely to bind to the typical metal, which has high ion bonding properties, the acidic alkyl phosphate ester has a too high acidity, and thus is likely to corrode the metal surface. The metal and the organic amine compound can increase the pH of the metal affinity compound and reduce the acidity thereof.

Examples of the metal include alkali metals such as Li, Na and K; alkaline earth metals such as Mg and Ca; aluminum; titanium; and zinc. These may be used alone or in a combination of two or more. Of these, Li and Ca are preferable from the viewpoint in which an adduct formed has more excellent compatibility with the base oil.

As the organic amine compound, an organic amine compound having 2 to 100 carbon atoms is preferable from the viewpoint of versatility and viscosity of an adduct formed. An organic amine compound having 4 to 22 carbon atoms is more preferable. More specific examples of the organic amine compound include octylamine, laurylamine, myristylamine, stearylamine, behenylamine, oleylamine, beef tallow alkylamine, hardened beef tallow alkylamine, aniline, benzylamine, cyclohexylamine, diethylamine, dipropylamine, dibutylamine, diphenylamine, dibenzylamine, dicyclohexylamine, triethylamine, tributylamine, dimethyloctylamine, dimethyldecylamine, dimethylstearylamine, beef tallow dimethylalkylamine, hardened beef tallow dimethylalkylamine, and dimethyloleylamine. These may be used alone or in a combination of two or more. Of these, octylamine and laurylamine are preferable from the viewpoint of versatility and viscosity of an adduct formed.

It is preferable that the content ratio of the adduct (a) to the adduct (b) in molar ratio is 1:9 to 9:1. Such a content ratio makes it possible to exhibit an effect of stably retaining the base oil on the metal surfaces of various metals in a well-balanced manner. When the ratio of the adduct (a) increases, the coordinate bonding properties are improved. On the other hand, when the ratio of the adduct (b) increases, the ion bonding properties are improved. The content ratio of the adduct (a) to the adduct (b) is preferably 2:8 to 8:2, and more preferably 3:7 to 7:3.

In the metal affinity compound, the amount of residual phosphate groups (P—OH groups) is determined by the ratio between the acidic alkyl phosphate ester, the azole compound, and the metal and/or the organic amine compound. When the ratio of the acidic alkyl phosphate ester increases, the amount of the residual phosphate groups (P—OH groups) increases, and the acidity increases (the pH decreases). When the ratio of the acidic alkyl phosphate ester decreases, the amount of the residual phosphate groups (P—OH groups) decreases, and the acidity decreases (the pH increases). If the acidity of the metal affinity compound increases, the bonding properties thereof for the transition metals decrease, and therefore, it is preferable to suppress the acidity to a low level. From this viewpoint, the pH of the metal affinity compound is preferably 4 or more, and more preferably 5.5 or more. On the other hand, from the viewpoint of maintaining the ion bonding properties, the pH of the metal affinity compound is preferably 9 or less, and more preferably 8 or less.

When the valence of the acidic alkyl phosphate ester is defined as $x^-$, the valence of the azole compound is defined as $y^+$, the valence of the metal and/or the organic amine compound is defined as $z^+$, the number of moles of the acidic alkyl phosphate ester is defined as 1, the number of moles of the azole compound is defined as m, the number of moles of the metal and/or the organic amine compound is defined as n, and $f=1 \times x - m \times y - n \times z$, the acidic alkyl phosphate ester is excessive in a range of $0<f<2$, and there are residual phosphate groups (P—OH groups). When $f=0$, a total of the azole compound and the metal and/or organic amine compound is equivalent to the acidic alkyl phosphate ester, and there are no residual phosphate groups (P—OH groups). Moreover, when $f<0$, the acidic alkyl phosphate ester runs short, and there are no residual phosphate groups (P—OH groups). It is preferable that $f \leq 0$ in order to increase the pH of the metal affinity compound.

The above-described metal affinity compound can be mixed with the base oil to form a surface treating agent.

The surface treating agent is constituted by an agent containing the metal affinity compound and the base oil. The surface treating agent covers the metal surface and prevents the corrosion of the metal. The surface treating agent contains the metal affinity compound, thus making it possible to stably retain the base oil on the metal surface. This effect can be exhibited for both transition metals (particularly copper) and typical metals (particularly tin).

Examples of the base oil include alkylbenzene, alkylnaphthalene, polybutene, mineral oil, synthetic ester, oil and fat, silicone oil, polyglycol, normal paraffin, isoparaffin, and polyether, or oil obtained by blending two or more of these compounds. Of these, mineral oil and paraffinic oil are preferable from the viewpoint of the thermal stability.

The amount of the metal affinity compound contained in the surface treating agent is preferably 3 mass % or more from the viewpoint of maintaining the density of an alkyl group formed on the metal surface, and more preferably 5 mass % or more. On the other hand, the amount thereof is preferably 90 mass % or less from the viewpoint of maintaining the thickness of the oil film, and more preferably 80 mass % or less.

It is preferable that the surface treating agent is in a liquid form (or in a fluid state) at −40° C. to 120° C. from the viewpoint of excellent application properties for the metal surface, and it is particularly preferable that the surface treating agent is in a liquid form or in a fluid state at 20° C. to 100° C. If $R_1$ of the acidic alkyl phosphate ester has a small number of carbon atoms such as less than 4 carbon atoms or only a metal is a component for forming an adduct with the acidic alkyl phosphate ester, for example, the metal affinity compound has poor compatibility with the base oil, and a mixture of the metal affinity compound and the base oil is not in a liquid form in the above temperature range, thus making it difficult to apply the mixture onto the metal surface. In this embodiment, an agent that is in a liquid form or in a fluid state at −40° C. to 120° C. is used as the surface treating agent.

When the surface treating agent is applied onto the surface of the metal member, the film thickness is preferably 30 μm or less from the viewpoint of preventing the stickiness of the surface and splash to other portions, and more preferably 15 μm or less. On the other hand, the film thickness is preferably equal to or greater than a predetermined thickness from the viewpoint in which a chipped portion is likely to be formed due to a mechanical load, heat, or the like, and an electrical resistance value is likely to be insufficient. Examples of the lower limit of the film thickness include 0.5 μm, 2 μm, and 5 μm.

Manufacturing Process

Next, an example of a process for manufacturing this embodiment will be described. It should be noted that the manufacturing process is not limited to the following description.

First, the first metal member 11 is formed by pressing, into a predetermined shape, the plate material 11B including a copper alloy in which the plated tin layer 11A is formed on the surface. Next, the second metal member 12 is formed by pressing a plate material including an aluminum alloy into a predetermined shape.

Next, the surface treating layer 14 is formed on the surface of the first metal member 11 by immersing the first metal member 11 in a surface treating agent and then air-drying it at room temperature.

Next, the first metal member 11 and the second metal member 12 are pressure-welded to each other by stacking the first metal member 11 and the second metal member 12 and then sandwiching them with a pair of jigs. Accordingly, the first metal member 11 and the second metal member 12 are electrically connected to each other (see FIG. 1). In this case, in the connection portion 13 where the first metal member 11 and the second metal member 12 are connected to each other, high pressure is applied by the jigs, and an agent that is in a liquid form or in a fluid state at −40° C. to 120° C. is used as the surface treating agent. Therefore, the surface treating agent is removed from the connection portion 13. Accordingly, no surface treating layer 14 is interposed between the first metal member 11 and the second metal member 12, and therefore, the reliability of the electrical connection between the first metal member 11 and the second metal member 12 is improved.

Operations and Effects of this Embodiment

In the electrical connection structure 10 of this embodiment where the first metal member 11 including copper (alloy) on which the plated tin layer 11A is formed and the second metal member 12 are electrically connected to each other, the surface treating layer 14 formed by applying the surface treating compound containing the metal affinity compound and the base oil is formed on the first metal member 11.

The lipophilic group of the metal affinity compound contained in the surface treating compound binds to the base oil. On the other hand, it is thought that the affinity group of the adduct (a) between an acidic alkyl phosphate ester and an azole compound contained in the metal affinity compound preferentially binds to copper included in the plate material 11B constituting the first metal member 11, and the affinity group of the adduct (b) between a metal and/or an organic amine compound and an acidic alkyl phosphate ester preferentially binds to tin contained in the plated tin layer 11A.

That is, with this embodiment, the surface treating layer 14 containing a base oil component is stably retained on the surface of the first metal member 11. Therefore, even when water adheres across the plate material 11B constituting the first metal member 11 and the plated tin layer 11A and across the first metal member 11 and the second metal member 12, it is possible to suppress the flow of the corrosion current. As a result, with this embodiment, it is possible to suppress the corrosion of the metal members 11 and 12 in the electrical connection structure 10 where the metal members 11 and 12 are electrically connected to each other.

It should be noted that in this embodiment, the second metal member 12 is a member made of a metal material (aluminum or an aluminum alloy) having an ionization tendency larger than that of the first metal member 11, and therefore, the effect of this embodiment (effect of suppressing the corrosion of the metal members) is exhibited.

Embodiment 2

An electrical connection structure 20 of Embodiment 2 according to the present invention will be described with reference to FIG. 2 to FIG. 4. In the electrical connection structure 20 of this embodiment, a terminal 21 (an example of the first metal member) that includes copper or a copper alloy and an electric wire 22 that includes a core wire 22A (an example of the second metal member) including a metal having an ionization tendency larger than that of copper are electrically connected to each other. Repetitions of the descriptions in Embodiment 1 are omitted.

Electric Wire 22

The electric wire 22 is obtained by covering the outer circumference of the core wire 22A with an insulating coating 22B made of a synthetic resin. A metal having an ionization tendency larger than that of copper can be used as the metal constituting the core wire 22A, and examples thereof include magnesium, aluminum, manganese, zinc, chromium, iron, cadmium, cobalt, nickel, tin, and lead, or an alloy thereof. In this embodiment, the core wire 22A includes aluminum or an aluminum alloy.

The core wire 22A according to this embodiment is a stranded wire obtained by twisting a plurality of metal thin wires. A so-called single-core wire made of a metal rod material may also be used as the core wire 22A. Since aluminum and an aluminum alloy have a relatively small specific gravity, the weight of the terminated electric wire 20 can be reduced as a whole.

Terminal 21

Figure 2:
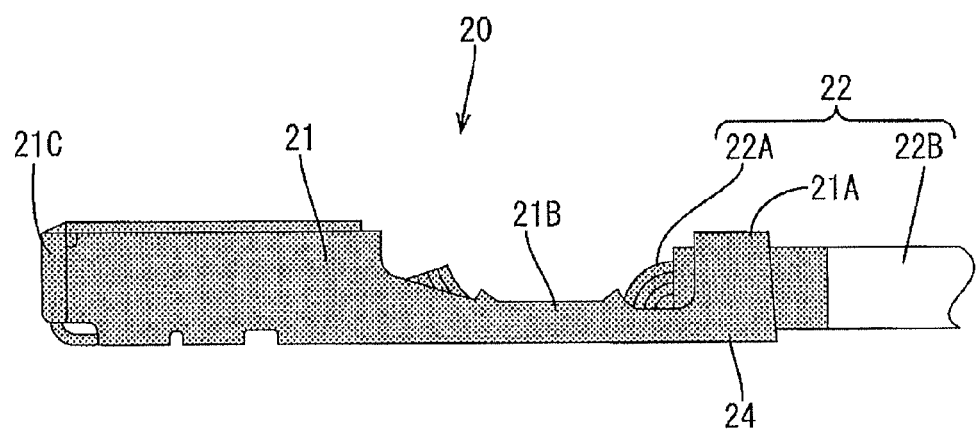
FIG. 2 is a side view showing an electrical connection structure according to Embodiment 2 of the present invention.

As shown in FIG. 2, the terminal 21 includes a wire barrel portion 21B to be connected to the core wire 22A exposed from the end portion of the electric wire 22, an insulation barrel portion 21A that is formed on the rear side with respect to the wire barrel portion 21B and holds the insulating coating 22B, and a main portion 21C that is formed on the front side with respect to the wire barrel portion 21B and into which a tab (not shown) of a male terminal is inserted.

Figure 3:
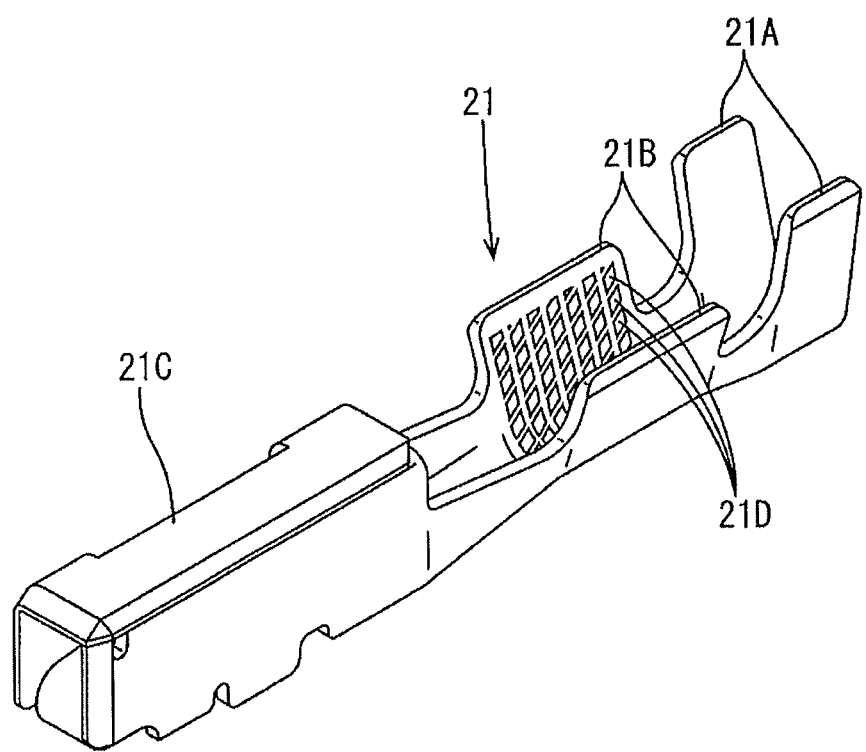
FIG. 3 is a perspective view of a terminal.

As shown in FIG. 3, a plurality of recessed portions 21D are formed in a region of the terminal 21 to which the core wire 22A exposed from the end portion of the electric wire 22 is to be connected. When the wire barrel portion 21B is crimped to the core wire 22A, the edges formed at hole edge portions of the recessed portions 21D come into sliding contact with the surface of the core wire 22A, and an oxidized coating formed on the surface of the core wire 22A is stripped. Accordingly, the metal surface of the core wire 22A is exposed. This metal surface comes into contact with the wire barrel portion 21B, and thus the core wire 22A and the wire barrel portion 21B (terminal 21) are electrically connected to each other.

The terminal 21 is obtained by pressing a plate metal material made of copper or a copper alloy into a predetermined shape. A plated tin layer (not shown) is formed on the front surface and the back surface of the terminal 21. The plated tin layer has a function of reducing a contact resistance between the core wire 22A and the wire barrel portion 21B. The plated tin layer is not formed on the end surface of the terminal 21, and the plate material including copper or a copper alloy is exposed.

In this embodiment, as shown in FIG. 2, a surface treating layer 24 is formed on the entire surface of the terminal 21. The surface treating layer 24 is shown as a shaded region in FIG. 2. That is, in this embodiment, the surface treating layer 24 is formed on the surface of the terminal 21 including the end surface of the terminal 21 (at least the end surface of the wire barrel portion 21B).

It should be noted that although the core wire 22A is exposed from the wire barrel portion 21B on the front side and the rear side with respect to the wire barrel portion 21B, the surface treating layer 24 is also formed on the surface of the core wire 22A.

Figure 4:
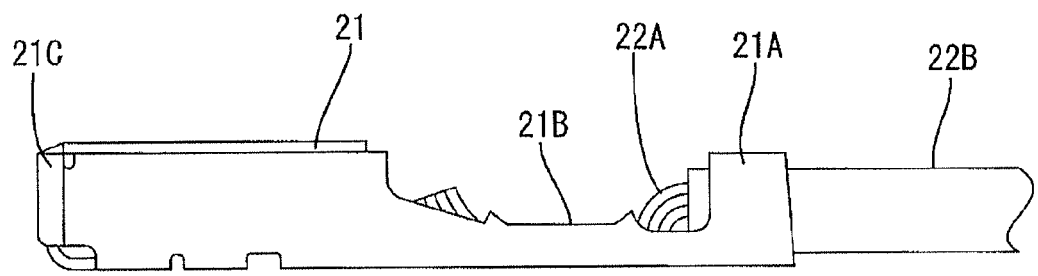
FIG. 4 is a side view of a terminated electric wire before the formation of a surface treating layer.

In this embodiment, for example, after the terminal 21 is crimped to the electric wire 22 into a state shown in FIG. 4, the surface treating layer 24 can be formed by immersing at least the terminal 21 and the core wire 22A exposed from the electric wire 22 into a surface treating agent and drying it.

Operations and Effects of this Embodiment

In the electrical connection structure 20 of this embodiment where the terminal 21 including copper (alloy) on which the plated tin layer is formed and the electric wire 22 are electrically connected to each other, the surface treating layer 24 formed by applying the surface treating compound containing the metal affinity compound and the base oil is also formed on the terminal 21 in the same manner as in Embodiment 1.

Accordingly, with this embodiment, the surface treating layer 24 containing a base oil component is stably retained on the surface of the terminal 21. Therefore, even when water adheres across a portion of the terminal 21 on which no plated tin layer is formed and the plated tin layer and across the terminal 21 and the electric wire 22, it is possible to suppress the flow of the corrosion current, thus making it possible to suppress the corrosion of the terminal 21 and the electric wire 22 in the electrical connection structure 20 where the terminal 21 and the electric wire 22 are electrically connected to each other.

Embodiment 3

Next, an electrical connection structure 30 of Embodiment 3 according to the present invention will be described with reference to FIG. 5. This embodiment has a structure in which a copper electric wire 32 that includes a copper core wire 32A (an example of the second metal member) including copper or a copper alloy and an aluminum electric wire 33 that includes an aluminum core wire 33A (an example of the second metal member) including aluminum or an aluminum alloy are connected to a spliced terminal 31. The outer circumference of the copper core wire 32A is covered with an insulating coating 32B made of a synthetic resin, and the outer circumference of the aluminum core wire 33A is covered with an insulating coating 33B made of a synthetic resin. It should be noted that repetitions of the descriptions in Embodiment 1 are omitted.

In this embodiment, the copper core wire 32A and the aluminum core wire 33A are electrically connected to each other using the spliced terminal 31. The spliced terminal 31 includes a wire barrel portion 31A that is crimped to both the copper core wire 32A and the aluminum core wire 33A so as to be wound around them. The spliced terminal 31 is constituted by a plate material including copper or a copper alloy, and a plated tin layer (an example of the first metal member) (not shown) is formed on its surface, but no plated tin layer is formed on its end surface.

After the copper core wire 32A and the aluminum core wire 33A are connected to the spliced terminal 31, a surface treating layer 34 is formed on the surfaces of the copper core wire 32A, the aluminum core wire 33A, and the spliced terminal 31 by immersing the spliced terminal 31, the copper core wire 32A, and the aluminum core wire 33A in a surface treating agent and drying it.

Figure 5:
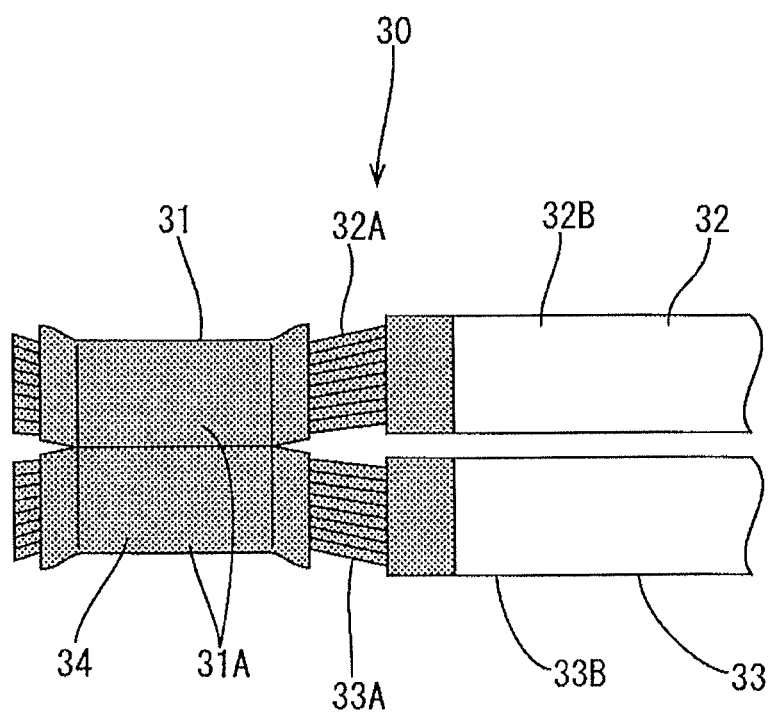
FIG. 5 is a plan view showing an electrical connection structure according to Embodiment 3 of the present invention.

In this embodiment, as shown in FIG. 5, the surface treating layer 34 is formed on at least the surface of the spliced terminal 31 including its end surface and the surfaces of portions of the copper core wire 32A and the aluminum core wire 33A exposed from the spliced terminal 31. The surface treating layer 34 is shown as a shaded region in FIG. 5.

Operations and Effects of this Embodiment

In the electrical connection structure 30 of this embodiment where the two electric wires 32 and 33 are electrically connected to the spliced terminal 31, in the same manner as in Embodiment 1, the surface treating layer 34 formed by applying the surface treating compound containing the metal affinity compound and the base oil is also formed on the spliced terminal 31 including copper (alloy) on which the plated tin layer is formed. Therefore, with this embodiment, it is also possible to suppress the corrosion of the spliced terminal 31 and the electric wires 32 and 33.

Embodiment 4

Figure 6:
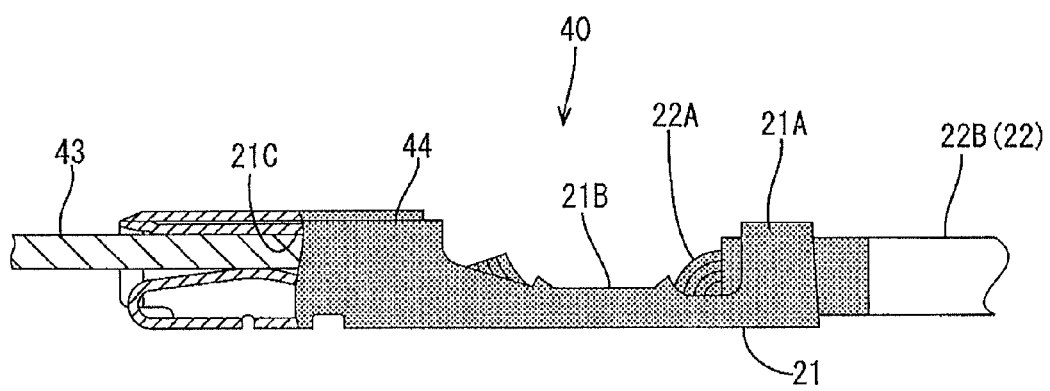
FIG. 6 is a plan view showing an electrical connection structure according to Embodiment 4 of the present invention.

Next, an electrical connection structure 40 of Embodiment 4 according to the present invention will be described with reference to FIG. 6. This embodiment relates to the electrical connection structure 40 where a first terminal 21 (an example of the first metal member) and a second terminal 43 (an example of the second metal member) that is mutually fitted to the first terminal 21 are electrically connected to each other. It should be noted that repetitions of the descriptions in Embodiment 1 are omitted.

The first terminal 21 is a so-called female terminal, and has a configuration similar to that of the terminal 21 of Embodiment 2. The first terminal 21 is constituted by a plate material including copper or a copper alloy, and a plated tin layer is formed on its surface. An electric wire 22 connected to the first terminal 21 has a configuration similar to that of the electric wire 22 connected to the terminal 21 of Embodiment 2, and includes a core wire 22A including aluminum and an aluminum alloy and an insulating coating 22B. Since the first terminal 21 and the electric wire 22 connected to the first terminal 21 are similar to those of Embodiment 2, they are denoted by the same reference numerals, and specific descriptions thereof are omitted.

In this embodiment, the surface treating layer is formed on at least the surface (including the end surface) of the first terminal 21 by immersing the first terminal 21 in a surface treating agent and then drying it. This makes it possible to suppress the elution of the second terminal 43 made of aluminum or an aluminum alloy due to electrolytic corrosion.

The second terminal 43 is a so-called male terminal provided with a tab and is constituted by a metal member including aluminum or an aluminum alloy that has an ionization tendency larger than that of copper. The second terminal 43 is inserted into a main portion 21C of the first terminal 21, and is electrically connected to the first terminal 21.

Since the surface treating layer is formed on the first terminal 21 by immersing the first terminal 21 in a surface treating agent and drying it in a state in which the electric wire 22 is connected to the first terminal 21, there is a possibility that the surface treating layer is formed in the main portion 21C of the first terminal 21 before the second terminal 43 is inserted thereinto. However, the surface treating layer is removed by the second terminal 43 inserted into the main portion 21C of the first terminal 21 sliding in the main portion 21C of the first terminal 21, and no surface treating layer is interposed in the connection portion where the first terminal 21 and the second terminal 43 are connected to each other. Therefore, the reliability of the electrical connection between the first terminal 21 and the second terminal 43 is improved.

Operations and Effects of this Embodiment

In the electrical connection structure 40 of this embodiment where the first terminal 21 including copper (alloy) on which the plated tin layer is formed and the second terminal 43 are electrically connected to each other, the surface treating layer formed by applying the surface treating compound containing the metal affinity compound and the base oil is also formed on the first terminal 21 in the same manner as in Embodiment 1. Therefore, with this embodiment, it is also possible to prevent the corrosion of the terminals 21, and to suppress the flow of leakage current between the first terminal 21 and the second terminal 43.

WORKING EXAMPLES

Although the present invention will be described by way of working examples hereinafter, the present invention is not limited to these working examples.

Synthesis of Metal Affinity Compound

Synthesis Example 1: OL-MBT-Li5

50 g (acid value of 0.163 mol) of oleyl acid phosphate ("Phoslex A18D" manufactured by SC Organic Chemical Co., Ltd., molecular weight of 467 (average), acid value of 183 mg KOH/g) and 50 ml of methanol were placed in a 500 ml flask, and were stirred at 50° C. to yield a uniform solution. A solution obtained by dissolving 10.86 g (0.0816 mol) of 5-methyl-1H-benzotriazole in 50 ml of methanol was gradually added thereto. The resulting clear solution was stirred for 30 minutes while keeping the temperature at 50° C. A solution obtained by dissolving 3.42 g (0.0815 mol) of lithium hydroxide monohydrate in 50 ml of methanol was further added thereto. The mixture was stirred for 10 minutes while keeping the temperature at 50° C. After it was confirmed that the resulting solution kept clear, methanol and generated water were distilled off under reduced pressure using a rotary evaporator. Furthermore, after the addition of 50 mL of toluene, the mixture was distilled off under reduced pressure in the same manner to distill generated water off by azeotrope, and then the product of interest, which was a yellow clear viscous substance, was obtained. OL-MBT-Li5 is the acidic alkyl phosphate ester in which 50% of the free phosphate groups form 5-methyl-1H-benzotriazole salt and the other 50% thereof form lithium salt.

Synthesis Example 2: OL-BT-Li5

A compound was synthesized in the same manner as in Synthesis Example 1, except that 9.72 g of 1,2,3-benzotriazole was added instead of 5-methyl-1H-benzotriazole. OL-BT-Li5 is the acidic alkyl phosphate ester in which 50% of the free phosphate groups form 1,2,3-benzotriazole salt and the other 50% thereof form lithium salt.

Synthesis Example 3: OL-BT-K5

A compound was synthesized in the same manner as in Synthesis Example 2, except that 4.57 g of potassium hydroxide was added instead of lithium hydroxide monohydrate. OL-BT-K5 is the acidic alkyl phosphate ester in which 50% of the free phosphate groups form 1,2,3-benzotriazole salt and the other 50% thereof form potassium salt.

Synthesis Example 4: OL-BT-Ca5

A compound was synthesized in the same manner as in Synthesis Example 2, except that 4.16 g of calcium dimethoxide was added instead of lithium hydroxide monohydrate. OL-BT-Ca5 is the acidic alkyl phosphate ester in which 50% of the free phosphate groups form 1,2,3-benzotriazole salt and the other 50% thereof form calcium salt.

Synthesis Example 5: OL-BT-Li3

A compound was synthesized in the same manner as in Synthesis Example 2, except that the amount of lithium hydroxide monohydrate was changed to 2.05 g. OL-BT-Li3 is the acidic alkyl phosphate ester in which 50% of the free phosphate groups form 1,2,3-benzotriazole salt, another 30% thereof form lithium salt, and the other 20% thereof remain the same.

Synthesis Example 6: IS-MBT-Li5

A compound was synthesized in the same manner as in Synthesis Example 1, except that isostearyl acid phosphate ("Phoslex A18OL" manufactured by SC Organic Chemical Co., Ltd., molecular weight of 487 (average), acid value of 178 mg KOH/g) was used instead of oleyl acid phosphate. IS-MBT-Li5 is the acidic alkyl phosphate ester in which 50% of the free phosphate groups form 5-methyl-1H-benzotriazole salt and the other 50% thereof form lithium salt.

Synthesis Example 7: IS-BT-Li5

A compound was synthesized in the same manner as in Synthesis Example 2, except that isostearyl acid phosphate (the same as the above) was used instead of oleyl acid phosphate. IS-BT-Li5 is the acidic alkyl phosphate ester in which 50% of the free phosphate groups form 1,2,3-benzotriazole salt and the other 50% thereof form lithium salt.

Synthesis Example 8: IS-BT-K5

A compound was synthesized in the same manner as in Synthesis Example 7, except that 4.45 g of potassium hydroxide was added instead of lithium hydroxide monohydrate. IS-BT-K5 is the acidic alkyl phosphate ester in which 50% of the free phosphate groups form 1,2,3-benzotriazole salt and the other 50% thereof form potassium salt.

Synthesis Example 9: IS-BT-Ca5

A compound was synthesized in the same manner as in Synthesis Example 7, except that 4.05 g of calcium dimethoxide was added instead of lithium hydroxide monohydrate. IS-BT-Ca5 is the acidic alkyl phosphate ester in which 50% of the free phosphate groups form 1,2,3-benzotriazole salt and the other 50% thereof form calcium salt.

Synthesis Example 10: IS-BT-Li3

A compound was synthesized in the same manner as in Synthesis Example 7, except that the amount of lithium hydroxide monohydrate was changed to 2.00 g. IS-BT-Li3 is the acidic alkyl phosphate ester in which 50% of the free phosphate groups form 1,2,3-benzotriazole salt, another 30% thereof form lithium salt, and the other 20% thereof remain the same.

Synthesis Example 11: EH-BT-Li5

A compound was synthesized in the same manner as in Synthesis Example 2, except that di-2-ethylhexyl acid phosphate ("Phoslex A-208" manufactured by SC Organic Chemical Co., Ltd., molecular weight of 322 (average), acid value of 172 mg KOH/g) was used instead of oleyl acid phosphate. EHBT-Li5 is the acidic alkyl phosphate ester in which 50% of the free phosphate groups form 1,2,3-benzotriazole salt and the other 50% thereof form lithium salt.

Synthesis Example 12: EH-BT-Ca5

A compound was synthesized in the same manner as in Synthesis Example 11, except that 3.92 g of calcium dimethoxide was added instead of lithium hydroxide monohydrate. EH-BT-Ca5 is the acidic alkyl phosphate ester in which 50% of the free phosphate groups form 1,2,3-benzotriazole salt and the other 50% thereof form calcium salt.

Synthesis Example 13: IS-BI-Li5

A compound was synthesized in the same manner as in Synthesis Example 6, except that 9.37 g of benzimidazole was added instead of 5-methyl-1H-benzotriazole. IS-BI-Li5 is the acidic alkyl phosphate ester in which 50% of the free phosphate groups form benzimidazole salt and the other 50% thereof form lithium salt.

Synthesis Example 14: IS-BI-Ca5

A compound was synthesized in the same manner as in Synthesis Example 13, except that 4.05 g of calcium dimethoxide was added instead of lithium hydroxide monohydrate. IS-BI-Ca5 is the acidic alkyl phosphate ester in which 50% of the free phosphate groups form benzimidazole salt and the other 50% thereof form calcium salt.

Synthesis Example 15: IS-MBTZ-Li5

A compound was synthesized in the same manner as in Synthesis Example 6, except that 13.27 g of 2-mercaptobenzothiazole was added instead of 5-methyl-1H-benzotriazole. IS-MBTZ-Li5 is the acidic alkyl phosphate ester in which 50% of the free phosphate groups form 2-mercaptobenzothiazole salt and the other 50% thereof form lithium salt.

Synthesis Example 16: IS-MBTZ-Ca5

A compound was synthesized in the same manner as in Synthesis Example 15, except that 4.05 g of calcium dimethoxide was added instead of lithium hydroxide monohydrate. IS-MBTZ-Ca5 is the acidic alkyl phosphate ester in which 50% of the free phosphate groups form 2-mercaptobenzothiazole salt and the other 50% thereof form calcium salt.

Synthesis Example 17: IS-TT-Li5

A compound was synthesized in the same manner as in Synthesis Example 6, except that 30.66 g of 1-[N,N-bis(2-ethylhexyl)aminomethyl]methylbenzotriazole (TTLX: manufactured by Johoku Chemical Co. Ltd.) was added instead of 5-methyl-1H-benzotriazole. IS-TT-Li5 is the acidic alkyl phosphate ester in which 50% of the free phosphate groups form TTLX salt and the other 50% thereof form lithium salt.

Synthesis Example 18: IS-TT-Ca5

A compound was synthesized in the same manner as in Synthesis Example 17, except that 4.05 g of calcium dimethoxide was added instead of lithium hydroxide monohydrate. IS-TT-Ca5 is the acidic alkyl phosphate ester in which 50% of the free phosphate groups form TTLX salt and the other 50% thereof form calcium salt.

Synthesis of comparative compound

Synthesis Example 19: MT-BT-Li5

A compound was synthesized in the same manner as in Synthesis Example 2, except that methyl acid phosphate ("Phoslex A-1" manufactured by SC Organic Chemical Co., Ltd., molecular weight of 119 (average), acid value of 707 mg KOH/g) was used instead of oleyl acid phosphate. MT-BT-Li5 is the acidic alkyl phosphate ester in which 50% of the free phosphate groups form 1,2,3-benzotriazole salt and the other 50% thereof form lithium salt.

Synthesis Example 20: IS-BT

A compound was synthesized in the same manner as in Synthesis Example 7, except that no lithium hydroxide monohydrate was added. IS-BT is the acidic alkyl phosphate ester in which 50% of the free phosphate groups form 1,2,3-benzotriazole salt and the other 50% thereof remain the same.

Synthesis Example 21: OL-Ca8

A compound was synthesized in the same manner as in Synthesis Example 4, except that no 1,2,3-benzotriazole was added and the amount of calcium dimethoxide was changed to 6.66 g. OL-Ca8 is the acidic alkyl phosphate ester in which 80% of the free phosphate groups form calcium salt.

Preparation of Surface Treating Agent

Working Examples 1 to 23, Comparative Examples 1 to 7

A surface treating agent was prepared by mixing each of the metal affinity compounds obtained in Synthesis Examples 1 to 21 and base oil in a predetermined proportion. Types of the base oil and the mixing proportions are as shown in Tables 1 and 2. It should be noted that surface treating agents of Comparative Examples 1 and 2 are constituted by only base oil.

It should be noted that PA5, YUBASE and PAO shown in the tables are as follows.
PA5: "Unipress PA5" manufactured by JX Nippon Oil & Energy Corporation
YUBASE: "YUBASE8" (liquid paraffin-based) manufactured by Exxon Mobil Corporation
PAO: "SPECTTRASYN40" (polyalphaolefin-based) manufactured by Exxon Mobil Corporation Measurement of pH The pH of each surface treating agent was measured. Each surface treating agent was suspended in pure water in a proportion of about 3% (w/v) by ultrasonic irradiation, and the pH of the suspension was measured using a pH meter equipped with a glass electrode.

f Value

An f value was calculated when the valence of the acidic alkyl phosphate ester is defined as $x^-$, the valence of the azole compound is defined as $y^+$, the valence of the metal is defined as $z^+$, the number of moles of the acidic alkyl phosphate ester is defined as l, the number of moles of the azole compound is defined as m, the number of moles of the metal is defined as n, and $f=l \times x - m \times y - n \times z$. It should be noted that if the valence of the raw material was indicated, this value was used as the valence of the acidic alkyl phosphate ester, and if the valence of the raw material was not indicated, the valence of the acidic alkyl phosphate ester was determined by an acid value measurement using KOH.

Evaluation Test 1

Evaluation of Fluidity

Each surface treating agent was placed in a glass bottle, the glass bottle was tilted under a heating condition at 70° C., and the surface treating agent was visually observed to confirm whether or not the surface treating agent had fluidity. A surface treating agent that was confirmed to have fluidity was evaluated as "Good", and a surface treating agent that was confirmed to have no fluidity was evaluated as "Poor".

Oil Film Retainability

A Cu plate or a Sn plate that had been cut into a strip shape of 1 cm×5 cm was immersed in each of the surface treating agents, and was irradiated with an ultrasonic wave at 50° C. for 5 minutes using an ultrasonic cleaner. Then, the Cu plate or Sn plate was removed from the surface treating agent. An Al plate was used as an anode electrode and the Cu plate or the Sn plate was used as a cathode electrode, and the electrodes were immersed in a 5% NaCl solution to measure a potential difference (corrosion current).

The smaller the potential difference is, the larger (thicker) the residual amount (film thickness) of the surface treating agent on the surface of the Cu plate or the Sn plate is, and it can be said that the surface treating agent has an excellent surface treating effect. On the other hand, the larger the potential difference is, the smaller (thinner) the residual amount (film thickness) of the surface treating agent on the surface of the Cu plate or the Sn plate is, and it can be said that the surface treating agent has a low surface treating effect.

The oil film retainability was evaluated under three conditions, that is, right after the Cu plate or the Sn plate was removed from the surface treating agent, after the Cu plate or the Sn plate removed from the surface treating agent was subjected to hot water treatment, and after the Cu plate or the Sn plate removed from the surface treating agent was subjected to heat treatment. It should be noted that the hot water treatment was performed by cleaning the Cu plate or the Sn plate removed from the surface treating agent in hot water at 80° C. under stirring for 1 hour, and then, the Cu plate or the Sn plate was air-dried overnight. The heat treatment was performed by heating the Cu plate or the Sn plate removed from the surface treating agent in a vertical position in an oven at 120° C. for 48 hours. The corrosion current value obtained by using an untreated Cu plate was 50 µA, and that obtained by using an untreated Sn plate was 2.5 µA. When a current value was less than one tenth of these values, it was determined that the oil film retainability effect was high.

TABLE 1

|  |  | pH | f value | Work. Ex. | | | | | | | | | | | | |
|---|---|---|---|---|---|---|---|---|---|---|---|---|---|---|---|---|
|  |  |  |  | 1 | 2 | 3 | 4 | 5 | 6 | 7 | 8 | 9 | 10 | 11 | 12 |
| Metal affinity compound | OL-MBT-Li5 | 7.0 | 0 | 30 | | | | | | | | | | | |
|  | OL-BT-Li5 | 6.8 | 0 | | 30 | | | | | | | | | | |
|  | OL-BT-K5 | 6.8 | 0 | | | 30 | | | | | | | | | |
|  | OL-BT-Ca5 | 6.5 | 0 | | | | 30 | | | | | | | | |
|  | OL-BT-Li3 | 5.8 | 0.304 | | | | | 30 | | | | | | | |
|  | IS-MBT-Li5 | 6.8 | 0 | | | | | | 30 | | | | | | |
|  | IS-BT-Li5 | 6.9 | 0 | | | | | | | 30 | | | | | |
|  | IS-BT-K5 | 6.9 | 0 | | | | | | | | 30 | | | | |
|  | IS-BT-Ca5 | 6.7 | 0 | | | | | | | | | 30 | | | |
|  | IS-BT-Li3 | 5.9 | 0.31 | | | | | | | | | | 30 | | |
|  | EH-BT-Li5 | 6.7 | 0 | | | | | | | | | | | 30 | |
|  | EH-BT-Ca5 | 6.7 | 0 | | | | | | | | | | | | 30 |
|  | IS-BI-Li5 | 6.8 | 0 | | | | | | | | | | | | |
|  | IS-BI-Ca5 | 6.7 | 0 | | | | | | | | | | | | |
|  | IS-MBTZ-Li5 | 7.2 | 0 | | | | | | | | | | | | |
|  | IS-MBTZ-Ca5 | 7.0 | 0 | | | | | | | | | | | | |

TABLE 1-continued

| | | pH | f value | | | | | | | | | | | | |
|---|---|---|---|---|---|---|---|---|---|---|---|---|---|---|---|
| | IS-TT-Li5 | 7.0 | 0 | | | | | | | | | | | | |
| | IS-TT-Ca5 | 6.9 | 0 | | | | | | | | | | | | |
| | MT-BT-Li5 | 7.0 | 0 | | | | | | | | | | | | |
| | IS-BT | 3.9 | 0.775 | | | | | | | | | | | | |
| | OL-Ca8 | 4.8 | 0.304 | | | | | | | | | | | | |
| Base oil | Nujol | | | 70 | 70 | 70 | 70 | 70 | 70 | 70 | 70 | 70 | 70 | 70 | 70 |
| | PA5 | | | | | | | | | | | | | | |
| | YUBASE | | | | | | | | | | | | | | |
| | PAO | | | | | | | | | | | | | | |
| | 70° C. fluidity | | | Good | Good | Good | Good | Good | Good | Good | Good | Good | Good | Good | Good |
| Cu plate | Right after | | | 1.1 | 0.8 | 1.5 | 0.7 | 1.4 | 1.7 | 1.7 | 1.4 | 1.1 | 1.7 | 2.0 | 1.8 |
| | Hot water treatment | | | 1.6 | 0.9 | 1.9 | 0.9 | 1.9 | 1.8 | 1.7 | 2.1 | 1.4 | 2.1 | 2.1 | 1.9 |
| | Heat treatment | | | 1.5 | 0.9 | 1.5 | 0.9 | 1.6 | 2.0 | 1.7 | 1.6 | 1.8 | 2.4 | 2.1 |
| Sn plate | Right after | | | 0.04 | 0.04 | 0.06 | 0.04 | 0.15 | 0.06 | 0.06 | 0.17 | 0.05 | 0.11 | 0.14 | 0.12 |
| | Hot water treatment | | | 0.08 | 0.07 | 0.15 | 0.07 | 0.18 | 0.07 | 0.08 | 0.19 | 0.06 | 0.18 | 0.15 | 0.14 |
| | Heat treatment | | | 0.09 | 0.07 | 0.09 | 0.07 | 0.18 | 0.07 | 0.07 | 0.17 | 0.08 | 0.14 | 0.16 | 0.13 |

| | | | f | Work. Ex. | | | | | | | | | | |
|---|---|---|---|---|---|---|---|---|---|---|---|---|---|---|
| | | pH | value | 13 | 14 | 15 | 16 | 17 | 18 | 19 | 20 | 21 | 22 | 23 |
| Metal affinity compound | OL-MBT-Li5 | 7.0 | 0 | | | | | | | | | | | |
| | OL-BT-Li5 | 6.8 | 0 | | | | | | | 10 | | | | |
| | OL-BT-K5 | 6.8 | 0 | | | | | | | | | | | |
| | OL-BT-Ca5 | 6.5 | 0 | | | | | | | | | | | |
| | OL-BT-Li3 | 5.8 | 0.304 | | | | | | | | | | | |
| | IS-MBT-Li5 | 6.8 | 0 | | | | | | | | | | | |
| | IS-BT-Li5 | 6.9 | 0 | | | | | | | | 10 | 30 | 30 | 30 |
| | IS-BT-K5 | 6.9 | 0 | | | | | | | | | | | |
| | IS-BT-Ca5 | 6.7 | 0 | | | | | | | | | | | |
| | IS-BT-Li3 | 5.9 | 0.31 | | | | | | | | | | | |
| | EH-BT-Li5 | 6.7 | 0 | | | | | | | | | | | |
| | EH-BT-Ca5 | 6.7 | 0 | | | | | | | | | | | |
| | IS-BI-Li5 | 6.8 | 0 | 30 | | | | | | | | | | |
| | IS-BI-Ca5 | 6.7 | 0 | | 30 | | | | | | | | | |
| | IS-MBTZ-Li5 | 7.2 | 0 | | | 30 | | | | | | | | |
| | IS-MBTZ-Ca5 | 7.0 | 0 | | | | 30 | | | | | | | |
| | IS-TT-Li5 | 7.0 | 0 | | | | | 30 | | | | | | |
| | IS-TT-Ca5 | 6.9 | 0 | | | | | | 30 | | | | | |
| | MT-BT-Li5 | 7.0 | 0 | | | | | | | | | | | |
| | IS-BT | 3.9 | 0.775 | | | | | | | | | | | |
| | OL-Ca8 | 4.8 | 0.304 | | | | | | | | | | | |
| Base oil | Nujol | | | 70 | 70 | 70 | 70 | 70 | 70 | 90 | 90 | | | |
| | PA5 | | | | | | | | | | | 70 | | |
| | YUBASE | | | | | | | | | | | | 70 | |
| | PAO | | | | | | | | | | | | | 70 |
| | 70° C. fluidity | | | Good | Good | Good | Good | Good | Good | Good | Good | Good | Good | Good |
| Cu plate | Right after | | | 1.9 | 1.7 | 1.4 | 1.3 | 0.8 | 0.7 | 0.9 | 1.7 | 1.8 | 1.8 | 1.7 |
| | Hot water treatment | | | 2.0 | 1.9 | 1.8 | 1.8 | 0.9 | 0.8 | 1.0 | 2.0 | 2.1 | 2.0 | 1.8 |
| | Heat treatment | | | 2.1 | 1.9 | 2.1 | 1.9 | 1.1 | 0.9 | 1.1 | 1.8 | 2.1 | 2.1 | 1.9 |
| Sn plate | Right after | | | 0.11 | 0.12 | 0.13 | 0.09 | 0.04 | 0.04 | 0.09 | 0.09 | 0.11 | 0.10 | 0.08 |
| | Hot water treatment | | | 0.14 | 0.17 | 0.15 | 0.14 | 0.07 | 0.08 | 0.09 | 0.11 | 0.15 | 0.15 | 0.09 |
| | Heat treatment | | | 0.14 | 0.18 | 0.17 | 0.14 | 0.08 | 0.08 | 0.09 | 0.11 | 0.16 | 0.16 | 0.09 |

TABLE 2

| | | | f | Comp. Ex. | | | | |
|---|---|---|---|---|---|---|---|---|
| | | pH | value | 1 | 2 | 3 | 4 | 5 |
| Metal affinity compound | OL-MBT-Li5 | 7.0 | 0 | | | | | |
| | OL-BT-Li5 | 6.8 | 0 | | | | | |
| | OL-BT-K5 | 6.8 | 0 | | | | | |
| | OL-BT-Ca5 | 6.5 | 0 | | | | | |
| | OL-BT-Li3 | 5.8 | 0.304 | | | | | |
| | IS-MBT-Li5 | 6.8 | 0 | | | | | |
| | IS-BT-Li5 | 6.9 | 0 | | | | | |
| | IS-BT-K5 | 6.9 | 0 | | | | | |
| | IS-BT-Ca5 | 6.7 | 0 | | | | | |
| | IS-BT-Li3 | 5.9 | 0.31 | | | | | |
| | EH-BT-Li5 | 6.7 | 0 | | | | | |
| | EH-BT-Ca5 | 6.7 | 0 | | | | | |
| | IS-BI-Li5 | 6.8 | 0 | | | | | |
| | IS-BI-Ca5 | 6.7 | 0 | | | | | |
| | IS-MBTZ-Li5 | 7.2 | 0 | | | | | |
| | IS-MBTZ-Ca5 | 7.0 | 0 | | | | | |
| | IS-TT-Li5 | 7.0 | 0 | | | | | |

TABLE 2-continued

| | | pH | f value | Comp. Ex. 1 | 2 | 3 | 4 | 5 |
|---|---|---|---|---|---|---|---|---|
| | IS-TT-Ca5 | 6.9 | 0 | | | | | |
| | MT-BT-Li5 | 7.0 | 0 | | | 30 | | |
| | IS-BT | 3.9 | 0.775 | | | | 30 | |
| | OL-Ca8 | 4.8 | 0.304 | | | | | 30 |
| Base oil | Nujol | | | 100 | | 70 | 70 | 70 |
| | PA5 | | | | | 100 | | |
| | YUBASE | | | | | | | |
| | PAO | | | | | | | |
| | 70° C. fluidity | | | Good | Good | Good | Good | Poor |
| Cu plate | Right after | | | 45.2 | 45.1 | 17.5 | 2.1 | 14.5 |
| | Hot water treatment | | | 49.0 | 48.8 | 21.6 | 2.4 | 14.4 |
| | Heat treatment | | | 46.2 | 48.5 | 29.4 | 2.8 | 18.0 |
| Sn plate | Right after | | | 1.90 | 2.26 | 1.31 | 2.10 | 0.15 |
| | Hot water treatment | | | 2.25 | 2.41 | 1.57 | 2.24 | 0.19 |
| | Heat treatment | | | 2.31 | 2.44 | 1.69 | 2.26 | 0.24 |

Results and Discussion

As shown in Table 1, the surface treating agents of Working Examples 1 to 23 were in a liquid state with fluidity at 70° C., and it was confirmed from the evaluation results of the oil film retainability that they could retain the base oil on the metal surfaces. Moreover, it was confirmed that the retainability was not deteriorated due to the hot water treatment and the heat treatment, and the effect was firmly exhibited on the metal surfaces.

In contrast, since the surface treating agents of Comparative Examples 1 and 2 were constituted by only the base oil, the evaluation results of the oil film retainability revealed that the corrosion current values were very large, and it seems that substantially no base oil was retained even right after the application onto the metal surfaces.

It seems that the surface treating agent of Comparative Example 3 had low compatibility with the base oil since the alkyl group of the acidic alkyl phosphate ester in the comparative compound was a methyl group and the number of carbon atoms was small. The evaluation results of the oil film retainability revealed that the corrosion current values were very large, and it seems that substantially no base oil was retained even right after the application onto the metal surfaces.

It seems that since the comparative compound in the surface treating agent of Comparative Example 4 was constituted by only the adduct between the acidic alkyl phosphate ester and the azole compound, the corrosion current value was large when the Sn plate was used, and the oil film retainability effect for the surface of Sn was low.

It seems that since the comparative compound in the surface treating agent of Comparative Example 5 was constituted by only the adduct between the acidic alkyl phosphate ester and the metal, the corrosion current value was large when the Cu plate was used, and the oil film retainability effect for the surface of Cu was low. Moreover, it was found that the fluidity was low at 70° C.

Figure 7:
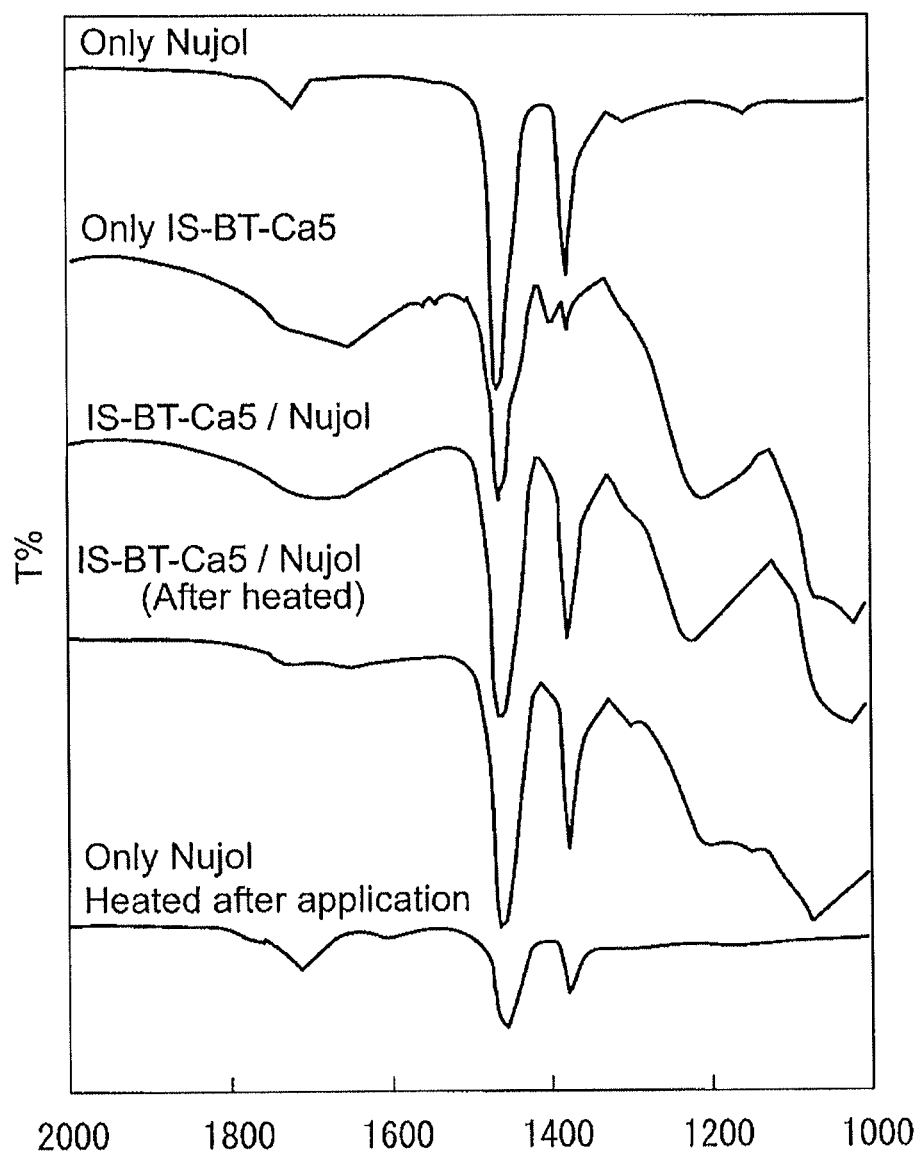
FIG. 7 shows IR spectra of various materials related to the evaluation of oil film retainability.

It should be noted that in order to confirm that the base oil of the surface treating agents of the working examples remained on the metal surface, the surface-reflection IR of a Cu plate onto which the surface treating agent of Working Example 9 was applied as an example was measured using a RAS method before and after the heat treatment. For comparison, the surface-reflection IR of a Cu plate onto which only the Nujol was applied was also measured before and after the heat treatment. Furthermore, for comparison, the surface-reflection IR of a Cu plate onto which only IS-BT-Ca5 of Synthesis Example 9 was applied and that was not subjected to the heat treatment was also measured. FIG. 7 shows the results. It should be noted that a symmetric deformation vibration of a methyl group at 1375 cm-1 was used as a reference to detect Nujol.

It was found from the results shown in FIG. 7 that peak sizes at 1375 cm-1 of Nujol containing IS-BT-Ca5 (IS-BT-Ca5/Nujol) were substantially the same before and after heated, whereas the peak size was reduced after heated in the case where only Nujol was used. Since there was no peak at 1375 cm-1 in the case where only IS-BT-Ca5, which contained no Nujol, was used, it can be said that Nujol containing IS-BT-Ca5 is retained even under heating conditions, and IS-BT-Ca5 serves as an oil film retaining material.

Since the metal affinity compounds of the present invention have an excellent function of retaining the base oil on the metal surface, it is found that use of the metal affinity compounds as the surface treating agents makes it possible to maintain the surface treating performance for a long period of time.

Evaluation Test 2

The resistance value of a fitting portion was measured using the first terminal and the second terminal of Embodiment 4. A male terminal provided with a tab having a width of 1 mm was used as the second terminal, and a female terminal that could be fitted to the first terminal was used as the first terminal.

The first terminal and the second terminal on which the surface treating layer was formed by immersing the first terminal to which an electric wire was connected and the second terminal in the surface treating agent of Working Example 1 and then drying it, and the first terminal and the second terminal onto which no surface treating agent was applied were prepared. The first terminal and the second terminal were fitted to each other, and the resistance value of the fitting portion was measured. The resistance value was measured with a four-terminal method.

The resistance value of the fitting portion using the first terminal and the second terminal onto which no surface treating agent was applied was 0.5 mΩ, whereas the resistance value of the fitting portion using the first terminal and the second terminal onto which the surface treating agent was applied was 0.6 mΩ.

These results revealed that the application of the surface treating agent hardly influenced the electrical connection.

Other Embodiments

The present invention is not limited to the embodiments, which have been described using the foregoing descriptions and the drawings, and, for example, embodiments as described below are also encompassed within the technical scope of the present invention.

(1) Although an example in which the surface treating layer 14 was formed on the surface of the first metal member 11 by immersing the first metal member 11 in a surface treating agent was shown in the above-mentioned embodiments, a method for forming a surface treating layer is not limited to this. For example, the surface treating agent may be applied onto the first metal member using a brush or sprayed onto the first metal member. Moreover, the adjustment of the coating amount, the uniformization of the appearance, and the equalization of the film thickness were performed with an air knife method or a roll squeeze method after coating treatment, immersing treatment, or spraying treatment with a squeeze coater or the like.

(2) Although an example in which the surface treating layer was formed on substantially the entire surface of the first metal member 11 was shown in the above-mentioned embodiment, the surface treating layer may be formed on only a portion of the surface of the first metal member 11.

(3) Although examples in which the surface treating layer was also formed on the core wire corresponding to the second metal member were shown in Embodiments 2 and 3, the surface treating layer need not be formed on the core wire.

LIST OF REFERENCE NUMERALS 10, 20, 30, 40 . . . Electrical connection structure
11 . . . First metal member
11A . . . Plated tin layer
11B . . . Plate material including copper (copper alloy)
12 . . . Second metal member
13 . . . Connection portion
14, 24, 34, 44 . . . Surface treating layer
21 . . . Terminal (first metal member)
21B . . . Wire barrel portion
21C . . . Main portion
22 . . . Electric wire
22A . . . Core wire (second metal member)
31 . . . Spliced terminal (first metal member)
31A . . . Wire barrel portion
32 . . . Copper electric wire
32A . . . Copper core wire (second metal member)
33 . . . Aluminum electric wire
33A . . . Aluminum core wire (second metal member)
41 . . . First terminal (first metal member)
43 . . . Second terminal (second metal member)

An aspect of the technique described in the specification may be configured as follows.

A content ratio of the adduct (a) to the adduct (b) in molar ratio may be 1:9 to 9:1. With this configuration, the surface treating layer comes into intimate contact with the metals in a well-balanced manner, and therefore, a corrosion preventing effect is ensured.

The pH of the surface treating agent may he set to 4 or more. With this configuration, in particular, an intimate contact effect is improved.

The azole compound may be at least one selected from pyrrole, imidazole, pyrazole, 1,2,3-triazole, 1,2,4-triazole, tetrazole, isoindole, benzimdazole, indazo 1H-benzotriazole, 2H-benzotriazole, imidazo[4,5b ]pyridine, indole, purine, pyrazolo[3,4-d ]pyrimidine, triazolo [4,5-d ]pyrimidine, and benzothiazole, or a derivative thereof.

With this configuration, in particular, a coordination force with respect to copper is excellent, and thus an excellent intimate contact effect is obtained.

The metal may be at least one selected from alkali metals, alkaline earth metals, aluminum, titanium, and zinc. With this configuration, the metal has an ionization tendency higher than that of tin, and therefore, excellent ion bonding properties for tin can be obtained.

The organic amine compound may be an organic amine compound having 2 to 100 carbon atoms. With this configuration, an adduct between the organic amine compound and an acidic alkyl phosphate ester can be made into a liquid form that has a viscosity with which the adduct can he handled at room temperature, and thus has an excellent handle ability.

The second metal member may be made of a metal material having an ionization tendency larger than that of the first metal member. With this configuration, even if the second metal member is made of aluminum or an aluminum alloy, it is possible to effectively suppress the corrosion of the metal members.

The surface treating layer may he in a liquid form or in a paste form under a temperature condition of $-40\,°$ C. to 120 $°$ C. With this configuration, the surface treating layer can be removed from the electrical connecting portion where the first metal member and the second metal member are electrically connected to each other by contact pressure or sliding, thus making it possible to improve the reliability of the electrical connection.

The first metal member may be a first terminal, and the second metal member may he a core wire of an electric wire that is electrically connected or connectable to the first terminal. With this configuration, it is also possible to prevent the corrosion of the metal members even in a connection structure where the terminal made of copper and the electric wire having a core wire made of aluminum (alloy) are connected to each other.

The first metal member may he a first terminal, and the second metal member may be a second terminal that is mutually fitted or fittable to the first terminal. With this configuration, it is possible to prevent the corrosion of the metal members even in a connection structure where the first terminal and the second terminal are connected to each other, and to suppress the flow of leakage current between the terminals.

The invention claimed is:

1. An electrical connection structure comprising:
 a first metal member including copper or a copper alloy, a plated tin layer being formed on at least a portion of the first metal member;
 a second metal member that is electrically connected or connectable to the first metal member; and
 a surface treating layer formed on a surface of the first metal member,
 wherein the surface treating layer is formed by applying a surface treating agent containing base oil and a metal affinity compound having a lipophilic group and an affinity group that has an affinity for metal, and the metal affinity compound contains:

an adduct (a) between an azole compound and an acidic alkyl phosphate ester including one or more of the compounds represented by General Formula (1):

and General Formula (2):

where $R_1$ represents an organic group having 4 or more carbon atoms; and an adduct (b) between a metal and/or an organic amine compound and an acidic alkyl phosphate ester including one or more of the compounds represented by General Formula (1) and General Formula (2).

2. The electrical connection structure according to claim 1, wherein a content ratio of the adduct (a) to the adduct (b) in molar ratio is 1:9 to 9:1.

3. The electrical connection structure according to claim 1, wherein a pH of the surface treating agent is set to 4 or more.

4. The electrical connection structure according to claim 1, wherein the azole compound is at least one selected from pyrrole, imidazole, pyrazole, 1,2,3-triazole, 1,2,4-triazole, tetrazole, isoindole, benzimidazole, indazole, 1H-benzotriazole, 2H-benzotriazole, imidazo[4,5-b]pyridine, indole, purine, pyrazolo[3,4-d]pyrimidine, triazolo[4,5-d]pyrimidine, and benzothiazole, or a derivative thereof.

5. The electrical connection structure according to claim 1, wherein the metal is at least one selected from alkali metals, alkaline earth metals, aluminum, titanium, and zinc.

6. The electrical connection structure according to claim 1, wherein the organic amine compound is an organic amine compound having 2 to 100 carbon atoms.

7. The electrical connection structure according to claim 1, wherein the second metal member is made of a metal material having an ionization tendency larger than that of the first metal member.

8. The electrical connection structure according to claim 1, wherein the surface treating layer is in a liquid form or in a paste form under a temperature condition of −40° C. to 120°C.

9. The electrical connection structure according to claim 1, wherein the first metal member is a first terminal, and the second metal member is a core wire of an electric wire that is electrically connected or connectable to the first terminal.

10. The electrical connection structure according to claim 1, wherein the first metal member is a first terminal, and the second metal member is a second terminal that is mutually fitted or fittable to the first terminal.

* * * * *